United States Patent [19]
Baxter

[11] Patent Number: 5,693,895
[45] Date of Patent: Dec. 2, 1997

[54] VERSATILE AIRBORNE PARTICLE IMPACTION SAMPLER

[76] Inventor: Daniel M. Baxter, 5290 Soledad Rd., San Diego, Calif. 92109

[21] Appl. No.: 607,141

[22] Filed: Feb. 26, 1996

Related U.S. Application Data

[63] Continuation-in-part of Ser. No. 276,627, Jul. 18, 1994, abandoned.
[51] Int. Cl.$^6$ .................................................. G01N 1/22
[52] U.S. Cl. .................. 73/863.22; 55/270; 73/28.05; 73/864.71
[58] Field of Search .................. 73/863.22, 863.23, 73/28.01, 28.04, 28.05, 863.21, 864.71; 55/270

[56] References Cited

U.S. PATENT DOCUMENTS

| | | | |
|---|---|---|---|
| 3,957,469 | 5/1976 | Nebash | 73/863.22 |
| 4,725,294 | 2/1988 | Berger | 73/863.22 |
| 4,972,957 | 11/1990 | Liu et al. | 73/28.05 |
| 5,201,231 | 4/1993 | Smith | 73/863.22 |
| 5,304,125 | 4/1994 | Leith | 73/28.05 |
| 5,437,198 | 8/1995 | John | 73/863.22 |

*Primary Examiner*—Hezron E. Williams
*Assistant Examiner*—Nashmiya Ashraf
*Attorney, Agent, or Firm*—John R. Duncan; Frank D. Gilliam

[57] ABSTRACT

An airborne particle impaction system and a particle impaction cell for use therewith. The cell includes a device for holding a removable planar support sheet with a tacky surface. The cell includes an inlet slit adjacent to a support sheet in the cell and an outlet opposite the sheet. A flexible tube connects the cell outlet to a vacuum pump. Air is drawn in the cell inlet slit, travels across the support sheet, around sheet edges and out the cell outlet. Particles in the air stream are forced by inertial forces to impact the support sheet, where they are retained by the tacky layer. The cell further includes a base having a floor, a rim around the floor and the cell outlet and a cover having a top surface bearing the slit and a lip configured to fit within and engage the base rim in a substantially air tight arrangement. A ledge around the base interior supports the corners of a polyhedral sheet. The support sheet is clamped between the cover lip and the ledge. Ideally, the slit exit is spaced closely (e.g. about 1 mm) to the tacky layer and air flow is at about 40 to 50 mph to cause particles having diameters greater than about 2 μm to impact and be captured by the tacky layer while allowing smaller particles to flow away with the air stream.

7 Claims, 1 Drawing Sheet

VERSATILE AIRBORNE PARTICLE IMPACTION SAMPLER

CROSS REFERENCE TO RELATED APPLICATIONS

This application is a continuation in part of U.S. patent application Ser. No. 08/276,627 filed Jul. 18, 1994, now abandoned.

BACKGROUND OF THE INVENTION

This invention relates in general to gathering samples of particles in the air and, more specifically, to a versatile self-contained slit impact airborne particle sampling apparatus for preferentially collecting particles in the greater than 2 μm size range.

Obtaining accurate samples of airborne particles such as fibers, pollen, mold spores, insect parts and other bioaerosols is necessary or desirable for a number of different purposes. Environmental professionals have a need to determine the presence and quantity of deleterious particles such as asbestos fibers in the air. Aero-biologists and allergists need to identify and quantify airborne pollen and mold spore concentrations for patient diagnosis. Epidemiologists are concerned with particles carrying bacteria, such as that responsible for Legionnaire's Disease, in air-conditioning systems and the like.

An increasing need for more versatile, convenient and effective apparatus for sampling airborne particles has developed in such areas as environmental air quality monitoring, fire and flood restoration, and industrial and occupational monitoring.

Filter sampling has long been used for particle and fiber analysis. Air is drawn through a microporous filter of the sort marketed by Millipore, Nuclepore and other companies. The filter is then examined under a microscope to determine the type and concentration of particles trapped on the filter media.

While effective for some purposes, filter sampling requires long sampling times to obtain reliable detection limits. The large filter areas require slow, careful examination by the microscopist performing the analysis. Relatively large filter areas, typically about 385 to 900 mm$^2$, are normally required to balance high sample flow rates, required velocity and resulting back pressures. Large particles such as pollen often do not remain attached to the filter, separating therefrom during transportation and handling. Further, special stains and refractive index liquids required to assist in particle identification are often incompatible with the filter media.

Slit or impact samplers, which direct air at relatively high velocity through a narrow rectangular slit against a tacky material have a number of advantages over filter sampling. A sample sufficient for analysis can be obtained in minutes rather than hours, the area to be examined is much smaller (approximately 16 mm$^2$) than the areas provided with filters and the tacky nature of the material used to collect the sample will retain large particles better than filters. Present slit type samplers are assembled in a housing containing a vacuum pump, a holder for a slide coated with a tacky material, such as a suitable grease, with a narrow rectangular slot in the housing adjacent to the tacky surface.

These devices can only be used in an upright or fixed position and cannot be easily used in confined or restricted spaces such as ventilation ducts because of their relatively large size. Electricity to power the vacuum pump must also be run to the sampling site, or a battery power source in the housing must be provided which further increases the bulk of the unit. These units are not weatherproof and are difficult to use in moist or exposed areas. Dust contamination can build up inside the case resulting in cross contamination of sample slides and will require regular and extensive cleaning between sample collection episodes. Further, slit geometry in prior collectors is such as to collect the undesired less than about 2 μm particles, making examination and analysis more difficult.

Upon completion of sampling the slides must be removed from the sampling device, packaged and shipped for analysis. Users must have specialized knowledge of sampling, decontamination, shipping and analysis procedures. Still, the opportunity for contamination, either inadvertent or intentional, is great.

With patients in hospitals, allergic persons while sleeping, workers in confined environments, etc., often have need for sampling near their faces to determine their actual exposure to allergens, toxic materials, etc. The large sampling devices of the prior art are very inconvenient for such uses, in particular where the person is mobile, because of their lack of easy portability.

Typical of prior particle collection devices are those described by Berger in U.S. Pat. No. 4,725,294 and Leith in U.S. Pat. No. 5,304,125. The Berger device uses a single, round nozzle that will produce a circular, gradually decreasing spot of collected particles that is much more difficult to analyze than a narrow line of particles and will tend to collect sub-micron particles that obscure the larger which are to be analyzed. Leith discloses a device using four spaced slits that are simple slots in a thin plate, which will not discriminate between larger particles of interest and sub-micron particles that are not of interest.

Thus, there is a continuing need for improved slit impact particle samplers that are capable of sampling under a variety of conditions in any desired area, including confined areas such as ventilation ducts, can sample in orientations other than horizontal, can be easily used for monitoring individuals, will preferentially collect particles in the greater than about 2 μm size range and produce a sharp, straight line of particles for easy examination, are resistant to contamination and may be used without extensive training.

SUMMARY OF THE INVENTION

The above noted problems, and others are overcome in accordance with this invention by an airborne particle impaction sampling system using a small, closed, sealable, sampling cell that can be located in a confined area connected by a long, flexible tube to a vacuum pump and other apparatus components.

The sampling cell comprises a two part housing, a cell base having a floor, an upstanding rim around the floor, means for holding a support plate above the floor and an outlet in the floor, and a cell cover having a top surface, a lip extending inwardly of the top surface for releasably engaging the cell base rim in an air tight relationship and a transverse slit across a portion of the top surface.

A flexible tube is connected between the cell base outlet and a vacuum pump. The pump draws air into the sampling cell in a direction preferably approximately perpendicular to the support plate. This cause particles in the air stream to impact the adjacent surface of the support plate and any receiving means thereon. The air flow path makes an approximately right angle turn at the support plate surface, then flows outwardly along the plate and around plate edges to the outlet, then through the tube to the pump.

The support plate is held in position in the cell by a clamping arrangement between the cell base and the cell cover. Preferably, a ledge is provided around the cell base inside the upstanding rim. The support plate is preferably a polyhedron having two closely spaced opposed faces and a plurality of straight edge faces. Corners formed by intersecting edge faces fit over the ledge and are clamped thereagainst by the cell cover lip when the cover is in engagement with the base. Optimally, the support sheet has a thickness of from about 0.25 to 1.0 mm and has from 3 to 8 edge sides. With a circular cell cross section, generally square cover sheets are most convenient.

If desired, other supports may be provided for the support sheet, so long as they clamp the sheet in place while providing uniform air flow around the sheet. For example, a plurality of pegs may be provided below the support sheet to, in cooperation with the ledge, support a thin sheet against deforming under high vacuum pump caused air flow. Alternately, the sheet could lie directly on the floor of the chamber, with a plurality of radial grooves in the floor extending from the outlet to the edge to act as air flow channels.

The support sheet is coated with a tacky material to bind and retain particles that impact thereagainst. Any suitable tacky material may be used, which preferably should be clear. Typical such materials include silicone grease, pressure sensitive adhesive tape, permanently tacky resins, etc.

Any suitable vacuum pump can be used. Preferably the pump should be capable of drawing from about 10 to 15 liters of air per minute. Typical vacuum pumps include the pump sold under the "Quiet Pump" by the Zefon Company.

Flexible vinyl tubing connecting the pump and sampling cell is preferred. However, any suitable flexible tubing may be used as desired. The sampling cell base and cover may be formed from any suitable material, such as acrylics, polycarbonate or other polymers which are not electrically conductive. These components can conveniently be formed by injection molding or any other suitable molding method.

For optimum results, the apparatus should capture nearly all particles in the greater than about 2 μm size range and pass through nearly all particles below that size range, in particular those particles having diameter in the sub-micron range. A uniform linear deposition geometry is critical for quantitative microscope analysis at magnifications ranging from about 100 to 1000X. The width of the deposition trace optimally is no more than about 1.1 mm in diameter to permit the entire width of the deposition trace to be visible at a standard magnification (200X) used to locate pollen grains. Slit size, geometry and distance of the collection media from the slit exit are important in simultaneously meeting these requirements.

For best results, the entrance of the V-shaped collection slit should be at least 10 times wider than the exit of the slit. The walls of the slit should taper smoothly and should have an included angle of from about 40° to 60°. The slit diameter may be up to about 1.5 mm, with the slit length at least about 10 times longer that the slit width. The media should be spaced about 0.5 to 1.5 mm beyond the slit exit. In order to provide the desired impaction of particles greater than about 2 μm into the collection media while allowing smaller particles to flow away with the airstream, the optimum air velocity is from about 40–50 mph.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figures 1, 2, 3, 4:
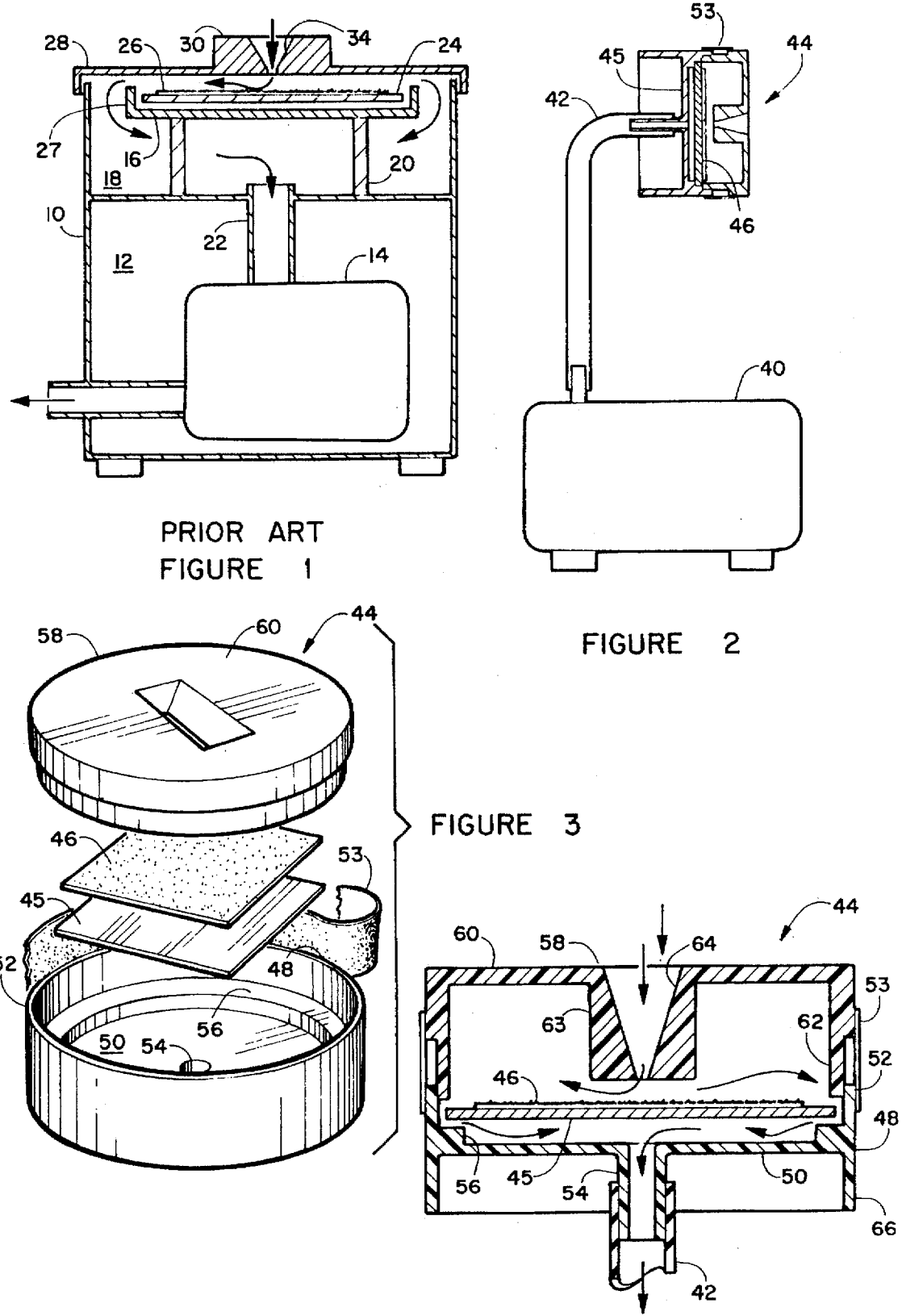
FIG. 1 is a schematic vertical section view through an airborne particle sampler of the prior art.
FIG. 2 is a schematic section view through an airborne particle sampler according to this invention.
FIG. 3 is an exploded view of the sampling cell used in this invention.
FIG. 4 is an axial slightly exploded section view through the sampling cell used in this invention.

A typical prior art airborne particle impaction sampler of the sort in use at present is shown in a schematic section view in FIG. 1. The sampler is a single unit, entirely contained within a housing 10. Lower volume 12 contains a vacuum pump 14. Pump 14 may be battery powered, in which case space is provided in housing 10 for batteries or may be powered by a separate battery pack or by 110 AC.

A platform 16 is contained in upper volume 18 of housing 10, typically supported by a plurality of legs 20 so that air can freely pass to pump inlet 22. Platform 16 carries a support sheet 24, (typically a 1 by 3 inch microscope slide) loosely laid on the top of the platform. A layer 26 of tacky material is applied to the top of support sheet 24.

The top of housing 10 is closed by a cover 28 which may loosely cover the top of upper compartment 18 or may be hinged or be otherwise removably secured thereto. A block 30 is secured over an opening in cover 28. A V-shaped slot 34 is provided through block 30, having an outer, entrance end and an inner, exit end adjacent to tacky layer 26.

When pump 14 is turned on, air is drawn into housing 10 through slot 34 and passes though the housing in the direction indicated by the arrows.

While generally useful in unconfined areas when attended by highly skilled personnel, the prior art system of FIG. 1 has a number of drawbacks. This device is not usable in small, confined spaces, such as ventilation ducts. It must be used in the horizontal position shown, since the support plate 24 is not secured in place and is subject to contamination from falling debris. After a support sheet 24 (typically a 3 by 1 inch glass microscope slide) with tacky layer 26 is installed, the unit must be moved careful, since tipping the unit could cause the tacky layer to contact and stick to the underside of cover 28. Once a sampling run is complete, the operator must remove cover 28, remove sheet 26 and package the sheet for shipping to an analysis site. There is great risk of contamination or other damage to the sample during this removal, packaging and shipping phase. Further, not all particles will adhere to layer 26 but may settle in corners and crevices, such as the space between sheet 24 and the upstanding edges 27 of platform 16. Therefore, very careful cleaning of upper compartment 18 and platform 16 must be done between sampling runs to prevent cross contamination by such settled particles that are stirred up as the housing is moved between test sites.

These problems with the prior art airborne particle samplers of the sort shown in FIG. 1 are overcome by the apparatus of this invention as shown in FIGS. 2–4.

As seen in FIG. 2, the apparatus basically comprises a vacuum pump 40, an elongated tube 42 and a sampling cell 44. Vacuum pump 40 may be placed at any convenient location; if necessary, well away from the actual sampling site, which might be a ventilation duct, a narrow area between machines or the like. Since, as detailed below, the support sheet 46 for the tacky sampling layer 46 is firmly held in place, sampling cell 44 may be positioned in any convenient orientation, including on its side, upright or inverted.

Tube 42 can have any suitable length. Where a great variation in tubing lengths is anticipated, a variable speed vacuum pump 40 could be used, so that air flow losses due to friction in very long tubes can be accommodated, providing substantially uniform air flow through sampling cell 44 despite tubing length variations.

As best seen in FIGS. 3 and 4, sampling cell 44 comprises a cell base 48 and a cell cover 58. While the circular configuration shown is preferred for convenience and ease of use, any other shape, such as square or rectangular, may be used, if desired.

Cell base 48 has a flat floor 50 and a peripheral upstanding rim 52. An outlet tube 54 is provided through floor 50, preferably at approximately the center of the floor. A ledge 56 is provided between the inner surfaces of rim 52 and floor 50 to hold support sheet 45. As seen in FIG. 3, the corners of support sheet 45 are engaged by ledge 56, leaving a space between the support sheet edges and rim 52 open for passage of air as indicated by the arrows in FIG. 4.

FIG. 4 is an axial section through exploded FIG. 3, showing cell base 48, cell cover 58 and support plate 45 slightly exploded for clarity, to schematically show the air flow path. FIG. 2 shows those components in the fully assembled position.

Cell cover 58 includes a top wall 60 having a peripheral lip 62 sized to fit within rim 52 of base 48. A transverse block 63 formed with top wall 60 has a transverse slit 64 having a V-shaped cross section slot ending in a narrow rectangular opening.

For optimum results in achieving preferential collection of particles having diameters greater than about 2 µm along a narrow straight line, the included angle between the walls of slot 34 is from about 40° to 60°, the walls are smoothly tapered, the outer, entrance end of slot 34 is at least about 10 times as wide as the width of the inner, exit end of the slit and the length of the slit is at least about 10 times the inner, exit end of the slit.

In use, a tube 42 is connected to outlet 54 and the assembled sampling cell 44 is placed at the desired sampling location, oriented in any desired attitude. The second end of tube 42 is secured to vacuum pump 40, which may be at any selected location including those well away from the sampling cell. As vacuum pump 40 runs, air enters at high velocity through slot 64, bends essentially 90° adjacent to tacky layer 46 and passes around the edges of support 45 to outlet 54. Inertial forces cause particles entering through slot 64 to impact tacky layer 46 and adhere thereto. For optimum preferential capture of particles having diameters greater than about 2 µm while allowing smaller particles to flow through, the diameter of the inner, exit slit should be up to about 1.1 mm and should be spaced about 0.5 to 1.5 mm from tacky surface 46, with airflow through the exit slit of from about 40 to 50 mph.

The pump is operated for the desired period and shut off. Sampling cell 44 is removed from tube 42, the openings are covered with caps and/or plugs, and taken to an analysis station for microscopic or other analysis of the captured particles.

For shipping or storage, the sampling cell can be placed in a conventional plastic bag to prevent contamination. The person operating the sampling assembly need not remove support 45 and tacky layer 46, so the greatest threat of contamination is eliminated. To limit intentional contamination, a seal, such as a cap, plug or a tape that would tear if removed, can be placed around the cell base-to-cover interface, to be removed only at the analysis laboratory. A frangible tape 53 is preferred, so that removal of the tape would cause tearing and disintegration, making reinstallation after tampering essentially impossible.

While certain preferred materials, dimensions and arrangements have been described in detail in conjunction with the above description of preferred embodiments, those can be varied, where suitable, with similar results. For example, tube 54 could include a right angle elbow adjacent to floor 50 and the lower skirt 66 could be notched so that tube 42 would enter through the notch, allowing the sample cell to be more easily positioned with slot 64 facing upward.

Other applications, variations and ramifications of this invention will occur to those skilled in the art upon reading this disclosure. Those are intended to be included within the scope of this invention as defined in the appended claims.

I claim:

1. An airborne particle impaction sampler which comprises:

a cell base having a floor, an upstanding rim around said floor, a continuous ledge lying in a single plane substantially parallel to said floor at the intersection of said floor and rim;

a removable polyhedral planar support sheet having a plurality of corners resting on said ledge;

said support sheet having from 3 to 6 substantially straight edges, all intersections between said edges having included angles no less than about 90° a cell cover having a top surface, a lip around said top surface for sliding insertion into said rim in a substantially air-tight relationship with said rim;

said lip when fully inserted into said rim clamping and resting directly on said support sheet corners between said lip and said ledge surface;

a layer of frangible tape covering edges of said cell cover and said rim so that said tape will tear if removed from said sampler;

a substantially straight transverse slit through said cell cover having an outer, entrance end exposed to the environment and an inner, exit end in close proximity to said support sheet where air flows through said inner end directly on to said sheet;

said slit having a generally V-shaped cross section;

said outer, entrance, end having a width at least 10 times the width of said inner, exit end;

a layer of tacky material on said support sheet adjacent to said inner exit slit end and spaced from about 0.5 to 1.5 mm from said inner, exit end; and an outlet through said floor for connection to a vacuum source for causing air flow inwardly through said outer, entrance end of said slit, out through said inner, exit end of said slit between said support sheet and said rim and out of said cell base.

2. The airborne particle impaction sampler according to claim 1 wherein said V-shaped cross section has an included angle of from about 40° to 60°.

3. The airborne particle impaction sampler according to claim 1 wherein air flow through said inner, exit end of said slit has a velocity of from about 40 to 50 mph.

4. The airborne particle impaction sampler according to claim 3 wherein said inner, exit end of said slit has a diameter and a spacing from said layer of tacky material such as to capture particles having diameters greater than 2 µm in said tacky material and exclude smaller particles.

5. The airborne particle impaction sampler according to claim 1 wherein said inner, exit end of said slit has a diameter of up to about 1.5 mm and said slit has a length at least about 10 times said diameter of said inner, exit end of said slit.

6. The airborne particle impaction sampler according to claim 1 wherein said slit has an outer, entrance end width of about 10 mm, an inner, exit slit width of about 1 mm and said inner, exit slit is spaced from said tacky layer about 1 mm.

7. The airborne particle impaction sampler according to claim 1 wherein said planar support sheet is square.

* * * * *